United States Patent [19]

Shepro et al.

[11] Patent Number: 5,466,667
[45] Date of Patent: * Nov. 14, 1995

[54] PROPHYLACTIC AND THERAPEUTIC METHODS FOR TREATING EDEMA WITH ANTAMANIDES

[75] Inventors: David Shepro, Boston, Mass.; J. Steven Alexander, Nashville, Tenn.

[73] Assignee: Trustees of Boston University, Boston, Mass.

[ * ] Notice: The portion of the term of this patent subsequent to Jan. 11, 2011, has been disclaimed.

[21] Appl. No.: 124,849

[22] Filed: Sep. 22, 1993

Related U.S. Application Data

[63] Continuation of Ser. No. 810,546, Dec. 19, 1991, abandoned, which is a continuation of Ser. No. 417,121, Oct. 4, 1989, abandoned, which is a continuation-in-part of Ser. No. 185,650, Apr. 25, 1988, abandoned.

[51] Int. Cl.$^6$ ............................. A61K 38/03; C07K 7/64
[52] U.S. Cl. ................. 514/11; 514/9; 514/870; 530/317; 530/321
[58] Field of Search ..................... 530/317, 321; 514/9, 11, 870

[56] References Cited

U.S. PATENT DOCUMENTS 5,278,143  1/1994  Shepro et al. ............................. 514/11

OTHER PUBLICATIONS

Welbourn et al., J. Appl. Physiol. vol. 70, pp. 1364–1368 (1991).
Rudinger, Peptide Hormones, Parsons (Ed.), J. Park Press, Baltimore, pp. 1–7 (1976).
Frimmer, Chem. Abstr. vol. 71, No. 99937m (1969).
Wieland et al., Crit. Rev. Biochem. vol. 5, pp. 185–260, (1978).

*Primary Examiner*—Christina Y. Chan
*Attorney, Agent, or Firm*—David Prashker

[57] ABSTRACT

Unique methods for treating edemas in living subjects are provided comprising administering an effective amount of an antamanide or an antamanide analogue to the subject. The methods offer prophylactic and therapeutic modes of treatment for both localized and systemic edemas. The antamanides and antamanide analogues may be applied topically or given parenterally; and may be employed with other diverse agents for treatment of both inflammatory and non-inflammatory edemas.

6 Claims, 1 Drawing Sheet

PROPHYLACTIC AND THERAPEUTIC METHODS FOR TREATING EDEMA WITH ANTAMANIDES

CROSS-REFERENCES

This application is a File Wrapper Continuation Application of U.S. patent application Ser. No. 810,546 filed Dec. 19, 1991, now abandoned; which was a continuation of U.S. patent application Ser. No. 417,121 filed Oct. 4, 1989, now abandoned; which was a Continuation-In-Part of U.S. patent application Ser. No. 185,650 filed Apr. 25, 1988.

GOVERNMENTAL SUPPORT

Research support for the present invention was provided by U.S. Public Health Service NHLB Grants Numbers HL16714 and HL33104.

FIELD OF THE INVENTION

The present invention is concerned with inflammatory and non-inflammatory associated edemas and is particularly directed to prophylactic and therapeutic methods for treating localized and systemic edemas.

BACKGROUND OF THE INVENTION

Edema is the term generally used to describe the accumulation of excess fluid in the intercellular (interstitial) tissue spaces or body cavities. Edema may occur as a localized phenomenon such as the swelling of a leg when the venous outflow is obstructed; or it may be systemic as in congestive heart faillure or renal failure. When edema is severe and generalized, there is diffuse swelling of all tissues and organs in the body and particularly pronounced areas are given their own individual names. For example, collection of edema in the peritoneal cavity is known as "ascites"; accumulations of fluid in the pleural cavity are termed "hydrothorax"; and edema of the pericardial sac is termed "pericardial effusion" or "hydropericardium". Non-inflammatory edema fluid such as accumulates in heart failure and renal disease is protein poor and referred to as a "transudate". In contrast, inflammatory edema related to increased endothelial permeability is protein rich and is caused by the escape of plasma proteins (principally albumin) and polymorphonuclear leukocytes (hereinafter "PMNs") to form an exudate.

Edema, whether inflammatory or non-inflammatory in nature, is thus an abnormality in the fluid balance within the microcirculation which includes the small arterioles, capillaries, and post-capillary venules of the circulatory system. Normal fluid balance and exchange is critically dependent on the presence of an intact and metabolically active endothelium. Normal endothelium is a thin, squamous epithelium adapted to permit selective, rapid exchange of water and small molecules between plasma and interstitium; but one which limits the passage of plasma proteins with increases in protein size.

The endothelial lining of all arterioles and venules, and most capillaries in the body, is of the continuous type, having an unbroken cytoplasmic layer with closely apposed intercellular junctions. Physiological studies [Renkin, E., *Circ. Res.* 41:735–743 (1977); Renkin, E., *ACTA Physiol. Scand. (Suppl.)* 463:81 (1979); Bottaro et al., *Microvasc. Res.* 32:389–398 (1986)] have demonstrated normal endothelial permeability for water and small molecules by the existance of water-filled small pores approximately 6 nanometers (hereinafter "nm") in radius or by slits about 8 nm wide. There is also believed to be a system of larger sized pores about 25 nm in radius which accounts for the small quantities of protein and other large solutes that normally cross the endothelial wall barrier.

A variety of different disturbances can induce a condition of edema. These include: an elevated venous hydrostatic pressure which may be caused by thrombosis of a vein or any other venous obstruction; hypoproteinemia with reduced plasma oncotic pressure resulting from either inadequate synthesis or increased loss of albumin; increased osmotic pressure of the interstitial fluid due to abnormal accumulation of sodium in the body because renal excretion of sodium cannot keep pace with the intake; failure of the lymphatics to remove fluid and protein adequately from the interstitial space; an increased capillary permeabiity to fluids and proteins as occurs in the inflammatory response to tissue injury; and an increased mucopolysaccharide content within the interstitial spaces.

Currently accepted therapeutic treatments for edema include those biogenic and synthetic pharmacological agents used to treat generalized inflammations, of which edema is merely one clinical manifestation. Such agents are said to inhibit the synthesis of pro-inflammatory (pro-phlogistic) metabolites; and can include such agents as aspirin, ibuprofen (salicylates and propionate derivatives), steroids, and anti-histamines. These agents have a wide scale of effectiveness and, in general, are most valuable in the treatment of minor inflammatory problems that produce only minor, localized edemas. There are few, if any, agents that are therapeutically effective in the treatment of severe, local and systemic edemas. Furthermore, as far as is known, there is no effective agent or admixture in present use as a prophylactic against these conditions.

It will be noted that until recently the endothelial cells, which constitute the microvasculature, were considered to be functionally passive in nature; in-vivo fluid exchange at the level of the microvasculature was therefore also considered to be functionally passive. Only in 1967 was it proposed that the passage of fluid and solute might occur at interendothelial junctions within the microvasculature, a routing also known as the "paracellular" pathway [Karnovsky, M. J., *J. Cell Bio.* 35:213–236 (1967)]. Subsequent investigations have focused principally upon other aspects of microvascular structural integrity such as: vesicle transport or transcellular channels which regulate the distribution of integral membrane proteins [Singer and Nicolson, *Science* 175:720–731 (1972)]; the presence of stress fibers intracellularly which are microfilament bundles composed of actin, myosin, and other contractile proteins [Fujiwara and Pollard, *J. Cell. Biol.* 71:848 (1976)]; the ability to disrupt endothelial actin cytoskeleton using cytochalasin B with a resulting increase in permeability for plasma proteins [Shahby et al., *Circ. Res.* 51:657–661 (1982)]; the demonstration that serotonin, histamine, and norepinephrine at physiological titers and concentrations inhibit endothelial cell movement [Bottaro et al., *Am. J. Physiol.* 248:C252–C257 (1985)]; the demonstration that serotonin and norepinephrine stimulate the assembly of stress fibers within endothelial cells whereas histamine produces stress fiber disassembly [Welles et al., *J. Cell. Physiol.* 123:337–342 (1985) and *Inflammation* 9:439–450 (1985)]; and, an in-vitro assay which demonstrates that endothelial cells are more effective as a barrier to impede labelled albumin diffusion when compared with cell cultures of vascular smooth muscle or fibroblasts [Bottaro et al., *Microvasc. Res.* 32:389–398 (1986)]. Such investigations have been directed at elucidating the mechanism of action present within the endothelial cytoskeleton; and identifying the role of the cytoskeleton in maintaining microvascular endothelial motility observable as junctional integrity. All these investigations and publications were therefore concerned with only the formulation of a theoretical model for mechanistic cytoskeleton controls and the accumulation of experimental evidence-to support the existence of such a mechanistic model.

Remote from and completely unrelated to these investigations regarding an active role model for endothelial cells in the microvasculature, were other research efforts directed towards the isolation and identification of the component substances of the poisonous green fungus *Amanita phalloides*. At least ten peptide-like substances of complex structure have been identified; most of these substances have proven to be extremely toxic liver toxins [*Liebig's Ann. Chem.*, volume 617, page 152, 1958; *Pharmacol. Reviews*, volume 7, page 87, 1959; *Liebig's Ann. Chem.*, volume 704, page 226, 1967].

Upon isolation and empirical analysis of the naturally occurring individual components of *Amanita phalloides*, investigators found that one of the naturally occurring substances, antamanide, was not only completely non-toxic of itself, but also was found capable of annulling the toxic effects of fetal doses of phalloidin and/or of protecting the liver completely when administered in therapeutic doses [Wieland et al., *Angew. Chem.* 80:208 (1968)]. Subsequently, investigations of this cyclic decapeptide, antamanide, have proceeded in two different directions: one research effort involved methods of synthesizing, purifying, and preparing analogues of antamanide. These investigations are exemplified by: U.S. Pat. Nos. 3,705,887 and 3,793,304; Anderson et al., *J. Am. Chem. Soc.* 88:1338–1339 (1966); Anderson et al., *J. Am. Chem. Soc.* 89:5012–5017 (1967); Wieland, T., *Angew. Chem.* (Internat. Edit. ) 7:204–208 (1968); Ovchinnikov et al., *Proc. Eur. Pept. Synp.* 11:403–415 (1973); Wieland et al., *Liebig's Ann. Chem.*, number 3, pages 371–380, 1977; Burgermeister et al. *Eur. J. Biochem.* 44:305–310 (1974); Tonelli, A. E., *Biochemistry* 12:689–692 (1973); Patel, D. J., *Biochemistry* 12:677–688 (1973); Ivanov et al., *Biochem. Biophys. Res. Comm.* 42:654–663 (1971); and Bir et al., *J. Peptide Protein Res.* 13:287–295 (1979)].

In comparison, the other investigative approach focused upon the physiological and pharmacological attributes of antamanide and its synthetic analogues. These investigations are exemplified by the following: Faulstich et al., *Hoppe Scylers. Z. Physiol. Chem.* 359:1162–1163 (1974); Ovchennikov et al., *Experientia* 28:399–401 (1972); Wieland et al., *Proc. Nat. Acad. Sci. U.S.A.* 81:5232–5236 (1984); Carle, I. L., *Proc. Nat. Acad. Sci. U.S.A.* 82:7155–7159 (1985); Munter, K. D. and H. Faulstich, *Biochim. Biophys. Acta* 860:91–98 (1986); Nielsen, O, *Acta Pharmacol. Toxicol.* 59:249–251 (1986); and Raymond et al., *Eur. J. Pharmacol.* 138:21–27 (1987).

In all of these published investigations and reports, the cyclic decapeptides comprising antamanide (also called "Phallin A") and its analogues were recognized solely as chemical agents capable at very low dosage of counteracting the effects of an absolutely fatal dose of phalloidin or of completely protecting the liver against such a fatal dose of phalloidin. Only recently was there any variation of these investigations into areas concerning cell proliferation and wound healing [Choi et al., *FASEB J.* 3:A290, Abstract No. 368 (1989)]. This Abstract was the first publication to suggest that antamanide might serve as a therapeutic agent in the treatment of vascular disease. Accordingly, the use of antamanide and the synthetic analogues remains primarily and predominently as an anti-toxin against the effects of phalloidin.

SUMMARY OF THE INVENTION

The present invention provides methods for therapeutically or prophylactically treating edema in a living subject. The method for therapeutically treating edema comprises the step of administering an effective amount of an antamanide or antamanide analogue to the subject after occurrence of the edema. The method for prophylactically treating edema comprises the step of administering an effective amount of an antamanide or an antamanide analogue to the subject prior to the occurrence of edema. Either methodology inhibits the permeability of fluid, macromolecules, and blood cells across the microvasculature thereby acting directly on the clinical edema and avoiding indirect metabolic cascades and pathways.

The prophylactic methodology can be employed in settings where iatrogenic-induced edema typically occurs such as with the use of clamps and/or tourniquets. The therapeutic methodology can be used to attenuate an inflammatory response as well as a non-inflammatory reaction.

BRIEF DESCRIPTION OF THE FIGURES

The present invention may be more easily and completely understood when taken in conjunction with the accompanying drawing, in which.

DETAILED DESCRIPTION OF THE PREFERRED EMBODIMENTS

Figure 1:
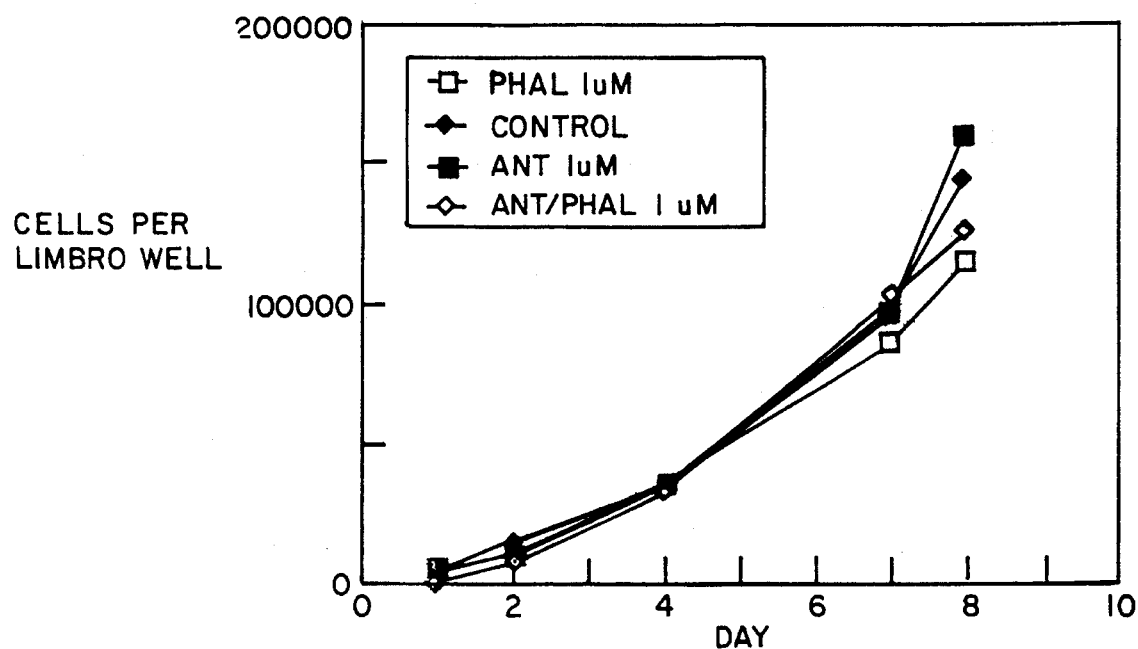
FIG. 1 is a graph illustrating the increase in cell proliferation as a consequence of antamanide, Phallin A, administration.

The present invention is the general methodology for prophylactically or therapeutically treating localized or systemic edemas in a living subject which comprises the step of administering an effective amount of an antamanide or an antamanide analogue to the living subject either before or after ocurrence of the edema in the subject. The broadest chemical definition of the class of compositions comprising antamanides and its analogues is provided by Formula I below:

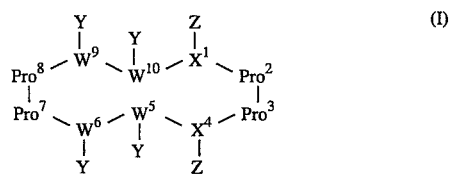

wherein

W individually is an amino acid having at least one ring structure comprised of not more than 6 carbon atoms;

X individually is an acyclic amino acid comprised of 3–9 carbon atoms;

Y individually may be omitted entirely, but when present is selected from the group consisting of hydrogen, a hydroxyl group, a halogen, a hydrocarbon, and a substituted hydrocarbon; and Z individually may be omitted entirely, but when present is selected from the group consisting of hydrogen, a halogen, a hydrocarbon, and a substituted hydrocarbon.

A preferred broad definition of the cyclic decapeptide compositions and structures comprising the class of antamanides and antamanide analogues is given by Formula II below:

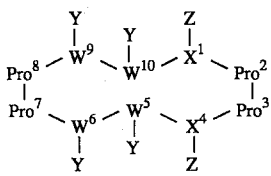
(II)

wherein

W individually is an amino acid having a benzene ring in its structure;

X individually is an amino acid selected from the group consisting of valine, alanine, leucine, and isoleucine;

Y individually may be omitted entirely, but when present is selected from the group consisting of hydrogen, a hydroxyl group, a halogen, a hydrocarbon moiety, and a substituted hydrocarbon moiety; and Z individually may be omitted entirely, but when present is selected from the group consisting of hydrogen, a halogen, a hydrocarbon moiety, and a substituted hydrocarbon moiety.

It will be recognized and appreciated that Formulas I and II respectively are presented using conventional chemical structure, format, and notations for amino acids and peptide organization as those found in Albert L. Lehninger's text, *Biochemistry, The Molecular Basis Of Cell Structure And Function*, 2nd edition, Worth Publishers, Inc., 1977—the text of which is expressly incorporated by reference herein. Moreover, Formulas I and II respectively by their definitions intend that all presently known and future embodiments of naturally occurring and non-naturally generated substances—which are by chemical formulation and structure one of those cyclic decapeptides forming the class of antamanides and antamanide analogues (including all substituted and derivatized forms)—lie within the scope of the present invention. However, the more desirable embodiments are those formulated and synthesized as described by U.S. Pat. Nos. 3,705,8897, 3,793,304, and 3,211,716—the texts of each being expressly incorporated by reference herein. These issued patents not only provide the best embodiments of naturally occurring and non-naturally generated antamanides; but also provide complete and detailed procedures and techniques for synthesizing and purifying antamanides and antamanide analogues for use in the present methodologies.

Accordingly, a preferred embodiment use for treatment of edema is the naturally occurring antamanide defined by Formula III, which is:

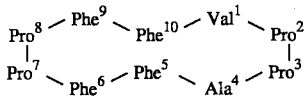
(III)

Another preferred embodiment of an antamanide useful for treating edemas is given by Formulas IVA–IVD:

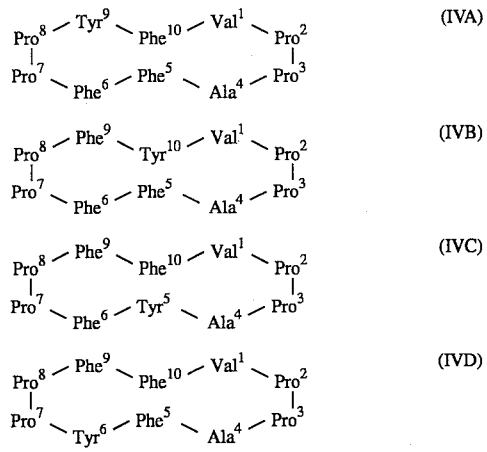

Within the various embodiments encompassed by Formulas I–IV inclusively, it will be recognized that the amino acids at the No. 1 position (typically L-valine) and at the No. 4 position (typically alanine) may be substituted by other amino acids. At a minimum, these other amino acids are acyclic—and by definition do not contain any ring structure within their composition. In addition, it is preferable that these amino acids also do not comprise a secondary nitrogen atom, a secondary carboxylic acid group, nor any sulfur atom. The preferred choices of "X" include L-leucine and L-isoleucine in addition to L-valine and L-alanine.

In comparison, the suitable amino acids at position Nos. 5, 6, 9, and 10 within the cyclic decapeptide structure each require the presence of a cyclic ring component. Preferred are hydrophobic side-chains such as a benzene ring of 6 carbon atoms. However, it is expected that other ring configurations ranging from 3–6 carbon atoms which are alternatively saturated or unsaturated in varying degree will also be useful. Accordingly, the broadest definition provided by Formula I requires the "W" positions only to be filled by an amino acid having at least one ring structure comprised of not more than 6 carbon atoms.

The given recitations of "Y" and "Z" identify commonly available chemical substitutions and derivatized forms for the general membership of the class comprising antamanides and antamanide analogues. The various substitutions and additions to the cyclic decapeptide structure are performed using commonly known syntheses and chemical reaction techniques. All of the embodiments of "Y" and "Z" are matters of personal choice and convenience well within the skills of the ordinary practitioners in this field.

The preferred methods for synthesizing the cyclic decapeptides comprising Formulas I–IV inclusive are those conventionally known and described in detail within U.S. Pat. Nos. 3,705,887, 3,793,304, and 3,211,716 respectively. The synthesis is preferably performed using acyclic decapeptides which are then cyclized into the overall cyclic form using conventional methods in peptide synthesis. In general, the cyclization from linear into cyclic form may take place at any position using the acyclic precursor peptide unit where an amino group and a carboxyl group are available for reaction. In the case of the amino acid proline, the imino group (HN=) may be present at the end of the chain instead of an amino group ($H_2N$—).

As noted in the above-cited patents, two processes are mainly involved, both of which however are suitable for general application and synthesis. In the first process, one end of the acyclic chain, preferably the carboxyl group, is applied in an activated form, while the amino reactive group has already been reversibly protected, or if this is not the case, must initially be protected. The amino protective group is then selectively split off in such a way that the amino group thus liberated is protected simultaneously by proteination. The deproteination of the reactive amino group by bases in highly dilute solution leads to cyclization.

The second general process employs a peptide zwitterion, the amino group of which is already present in proteinated condition. By activation of the carboxyl group and the addition of a base in diluted solution, or by addition of a dehydrating agent to the peptide zwitter ion, the cyclic end-product is also obtained in one step. Both of the general cyclization methods are performed in relatively great dilutions in order to suppress di- and poly-condensations.

In-vivo treatment with antamanides and antamanide analogues is intended to be a general methodology for treatment of edemas in living subjects, particularly humans. The scope of effective treatment using the present invention includes: both prophylactic and therapeutic applications; treatment of localized or systemic edemas; and treatment given independently or in combination with other medical and/or surgical modalities. The present invention is useful and effective with any one or any combination of these parameters.

Any of the antamanides or antamanide analogues encompassed by Formulas I–IV respectively may be administered to the living subject by one of two different routes: topically by direct application to the skin of the subject; and parenterally by injection or perfusion. If the antamanide is to be applied topically, the cyclic decapeptide can be admixed in a i pharmacologically inert topical carrier such as a gel, an ointment, a lotion, or a cream; and includes such carriers as water, glycerol, alcohol, propylene glycol, fatty alcohols, triglycerides, fatty acid esters, or mineral oils. Other possible topical carriers include liquid petrolatum, isopropylpalmitate, polyethylene glycol, ethanol, polyoxyethylene monolourate in water, sodium lauryl sulfate in water, and the like. Other materials such as anti-oxidantts, humectants, viscosity stabilizers, and the like may also be added as desired or necessary. In addition, it is expected (and in many instances desirable) that the antamanide be disposed within devices placed upon, in, or under the skin; such devices include patches and implants which release the active material into the skin or body either by diffusion or by an active release mechanism.

Alternatively, if the antamanide or antamanide analogue is to be given parenterally, it is expected that the compositions be prepared in sterile form; in multiple or single dose formats; and dispersed in a fluid carrier such as sterile physiological saline or 5% dextrose solutions commonly used with injectables.

In general, the concentration of the chosen antamanide or antamanide analogue (employed independently or combined with other substances) which may be effectively employed for prophylactic and/or therapeutic treatment of living subjects is expected to be: for topical applications, a range concentration from about 1–10 micrograms (hereinafter "ug") per gram of topical carrier. For intravenous, perfusion and other parenteral administration, a concentration range of from about 1.0 micromolar—0.1 micromolar per $L^{-1}$ of blood.

In addition, when the chosen antamanide or antamanide analogue is employed for prophylactic or therapeutic treatment of an edema which is a coincidental characteristic of an inflammatory reaction, it is most desirable that the cyclic decapeptide be administered in admixture with a variety of anti-inflammatory compounds. These include: aspirin, ibuprofen, thromboxane synthase inhibitors; receptor antagonists for the thromboxanes; prostacyclin-type agents; steroids; and superoxide and free radical scavengers.

A major advantage of the present invention is its ability to prophylactically or therapeutically treat edema, either at localized sites or systemically. To demonstrate the variety of uses and clinical circumstances in which the present methodology can be beneficially employed, a representative, but incomplete listing is provided by Table I below.

Table I (a) Topical Applications
   (1) Treatment of second and third degree burns
   (2) Skin cancer such as malignant melanoma and Kaposi's sarcoma
(b) Intravenous Applications
   (1) Skin flaps— modify swelling and maintain perfusion (prevention)
   (2) Trauma—modify swelling following fractures, crush injuries; prevent critical reduction in blood flow due to "compartment syndrome" in arms and legs (treatment)
   (3) Tourniquet use during extremity surgery to minimize reperfusion swelling (prevention)
   (4) Revascularization following occlusion of the coronary circulation (by fibrinolytic therapy or coronary artery bypass surgery); renal arterial occlusion; ileo-femoral occlusion (prevention)
   (5) Organ transplantation—treatment of donor and recipient to minimize swelling of the transplanted organ, thereby preserving function (prevention)
   (6) Low flow states associated with hemorrhage and sepsis—to prevent generalized edema; to prevent renal cortical-medulary swelling, reduction of blood flow and acute tubular necrosis (treatment)
   (7) Adult respiratory distress syndrome (ARDS) to prevent its occurrence that is permeability pulmonary edema in the following settings (treatment):
      (a) Lung contrusion
      (b) Acid aspiration
      (c) Smoke inhalation
      (d) Reperfusion of ischemic tissue:
         (1) lower torso
         (2) gastro-intestinal tract
      (e) Septicemia and other severe infections of the chest or abdomen
      (f) Pancreatitis
   (8) Burn edema—to minimize fluid loss into the second or third degree burn (treatment)
   (9) Ascites and pleural effusion secondary to inflammation or tumor seeding of the peritoneal or pleural spaces (treatment)
   (10) Arthritis—osteo and rheumatoid, to prevent joint swellings and effusions (treatment)
(c) Intraarticular
   Treatment of inflammatory edema of osteoarthritis and rheumatoid arthritis (treatment)
(d) Intrapleural/Intraperitoneal
   Treatment of pleural effusions and ascites secondary to inflammation or tumor nodules
(e) Rectal
   Enemas to be used to treat ulcerative colitis (treatment)
(f) Endodontics
   Prevention of post-surgical inflammatory permeability such as occurs in root canal procedures (treatment)

To demonstrate the efficacy and value of the novel methods comprising the present invention for prophylactic and/or therapeutic treatment of localized and systemic edemas, a variety of experiments will be described. It will be clearly understood, however, that these experimental examples are merely representative of the general conditions, uses, and advantages provided by the present invention; and serve merely to illustrate the variety of operative conditions and divergent applications with which the methods can be usefully employed. Under no circumstances, however, are the specific test conditions or empirically obtained results to be deemed as restricting or limiting the present invention in any manner.

EXPERIMENTAL SERIES

For experimental purposes, a single cyclic decapeptide defined by Formula III above was empirically evaluated. The embodiment is the naturally occurring form produced and isolatable from the *Amanita phalloides* fungus. Its amino acid sequence comprises L-valine at the No. 1 position; L-alanine at the No. 4 position; L-phenylalanine at position Nos. 5, 6, 9, and 10; and L-proline at position Nos. 2, 3, 7, and 8. For ease of description and for clarity of presentation, this embodiment will be termed "Phallin A" in accordance with conventional practice and nomenclature.

Experiment 1

Non-Toxic Effects

Cell Preparation, Culture, and Harvesting

Bovine abdominal aortas were clamped and tied in-situ and dissected free of the supporting adventitia. Aortas were transported from the abbatoir on ice. Endothelial cells were harvested by gentle ablation of the endothelium following the technique of Shepro et al. [*Anat. Rec.* 178:523 (1974)]; digested with 0.1% collagenase; and then pelleted and seeded onto 100 mm diameter tissue culture dishes using conventional techniques. The cell medium consisted of DULBECCO'S MODIFIED EAGLES'S MEDIUM medium (hereinafter "DME") at pH 7.4 supplemented with 10% fetal calf serum (hereinafter "FCS"), 0.1% of penicillin, 0.7% streptomycin, 0.1% amphotericin, and 0.1% glutamine. The cell media was replaced every 3 days. The cells were incubated at 37° C. in a 10% carbon dioxide, 90% ambient atmosphere (100% humidified). The isolation procedure, cobblestone morphology, positive uptake of DiI-acetylated low density lipoprotein and positive staining for the presence of factor VIII related antigen, document and prove that the cells in culture were in fact bovine aortic endothelial cells (hereinafter "BAEC").

Microfilament and Cell Surface Area Measurement

To demonstrate the effect upon endothelial cell shape, BAEC were seeded onto 1.2 centimeter glass coverslips and allowed to grow to 50% confluency in the conventional manner. This amount of confluency permits excellent visualization of cell spreading and stressed fibers. Individual confluent layers of cells were then treated with 1 uM Phallin A for 30 minutes duration; then fixed in 3.7% phosphate-buffered formaldehyde (pH 7.4) for 15 minutes. The cells on each coverslip were then permeabilized in extraction buffer (composed of 0.5M KCl, 1% triton X-100, 10 mM $MgCl_2$, and 1 mg/ml tosyl-arginine methyl ester (hereinafter "TAME"); 17 ug/ml toluene-sulfonyl fluoride (hereinafter "TSF"); and 0.25 mg/ml DNAse 1 in PBS for a period of 10 minutes. Subsequently, this extraction buffer was removed and the cells washed three times in sequence with PBS. The cells were then stained with Rhodamine-phalloidin (an F-active specific fluorescent probe, Molecular Probes, Inc., Junction City, Oreg.) at 1 unit/200 ul per coverslip for 39 minutes duration. Subsequently, the coverslips were washed five times consecutively in PBS; mounted in a 1:1 ratio mixture of PBS/glycerol; and sealed. The cultured cells on each coverslip were illuminated for fluorescence microscopy. The results showed that endothelial cells treated with Phallin A demonstrate an increased surface area and cell perimeter, the roundness of a cell being expressed as a ratio of cell perimeter to area. When BAEC are treated with 1.0 uM Phallin A, the exposed cells do not alter in proliferation and the ratio of cell perimeter to cell area diminishes as graphically illustrated by FIG. 1. For comparative purposes, 1.0 uM of phalloidin (also known as Phallin B) or a mixture of Phallin A and Phhallin B, and PBS alone as the control was similarly evaluated. As seen by FIG. 1, the Phallin A treated cells undergo substantial flattening and border extension in a manner comparable to the other agents and controls tested. Clearly, the use of Phallin A at concentrations of $10^{-6}$ to $10^{-7}$M is non-toxic to the cultured endothelial cells.

Experiment 2

Improvement Of Endothelial Barrier Function

Microcarrier Bead Culture

Bovine aortic endothelial cells (BAEC) were prepared, cultured, and harvested as described within Experiment 1. Subsequently, BAEC were subcultured a maximum of three times before seeding onto CYTODEX 3 microcarrier beads (Pharmacia, Inc. ). Microcarrier beads were suspended in cell media at a concentration of 40,000 microcarriers per milliliter. Beads were suspended by stirring, using a magnetic stirrer. BAEC were seeded onto the beads at the minimum density of 15 cells per bead and allowed to reach confluency. Subsequently, BAEC covered beads were allowed to incubate for 6 days post-confluency to obtain near maximum barrier function of the cell monolayers on the beads. After this incubation period, the BAEC covered beads were ready for use within permeability experiments. The ability of BAEC to form a functional barrier to the exchange of different marker substances between the bead interior and the surrounding media was tested in accordance with the methods of Boiadjeva et al. [*Lab. Invest.* 50:239–246 (1984)] as modified by Bottaro et al. [*Micrvasc. Res.* 32:389–398 (1986); see also Alexander et al. (1988).

Preparation of Permeability Assay Media

The identifying marker for permeability transfer between the bead interior of BAEC-covered beads and the surrounding culture medium was a conjugate of trypan blue dye and bovine serum albumin (hereinafter "TBA"). The molecular weight of this TBA identifying marker has been reported in the literature as being 100,000 daltons and has been demonstrated to be a useful identification marker for paracellular exchange. The TBA solution was prepared as a 2 x concentrate in PBS (pH 7.4) and sterilely stored at 4° C. until required for use. The final concentration of TBA in the surrounding cell culture medium was 0.2 trypan blue and 0.4% albumin in all instances.

Permeability Assay Procedure

BAEC barrier function was measured by TBA uptake per bead; therefore, it is necessary to standardize the number of beads per milliliter. CYTODEX 3 beads are composed of cross-linked dextrans and were standardized using an assay for total carbohydrate content of a 50 microliter (hereinafter "ml") aliquot of bead suspension using the Kochert method [*The Handbook Of Psycological Methods* (J. A. Hellebust and J. S. Craigie, editors), Cambridge University Press, Cambridge, 1978, pages 95–97]. In brief, the standardization utilized 50 ul bead samples which were dissolved in 5 ml of concentrated sulfuric acid for 15 minutes and then combined with 2 ml of 2.25% phenol. This produced a colored reaction product which absorbed light at 485 nm. Standard curves for absorbance as a function of bead concentration provides a linear relationship as a basis for comparison and extrapolation. Test samples were then compared with the standard curve to assess bead number per vial or cuvette. Controls for each test sample consisted of untreated BAEC-covered beads to assess the maximum possible uptake of TBA in the absence of other treatments.

BAEC barrier function was then assessed in the following manner: 3.0 ml of BAEC-covered microcarrier beads at a density of 40,000 beads per milliliter were aliquotted into a 4.5 ml test vial in duplicate. The TBA and the substance under test were then added to the culture medium. Alternately, beads could be pretreated with the substance under test prior to the addition of TBA. Vials containing the BAEC-covered beads were agitated and maintained under proper culture conditions. At preselected time intervals, triplicate 150 ul aliquots of the BAEC-covered beads were then removed from each vial and placed on a cushion containing a 3:1 ratio mixture of dibutyl/dioctyl-pthalate. The cell suspension was then centrifuged for 30 seconds at 15,000 x gravity. Centrifugation effectively terminates the TBA uptake by the beads by separating the dye mixture from the beads. The dye concentration in the supernatant after centrifugation was assayed by mixing 100 ul of the supernatant with 900 ul of distilled water and measuring the absorbance of the fluid at 595 nm.

This assay procedure uses colorimetry to measure TBA dye absorbance by the beads. If a test substance reduces BAEC barrier function, the beads would take up more dye in comparison to the controls; and the supernatant would then contain less dye in comparison with controls. Conversely, if a test substance increases barrier function, this would cause a reduced uptake of dye by the beads, and the dye concentration of the supernatant would be greater than that of the controls.

Increases In Barrier Function

Figure 2:
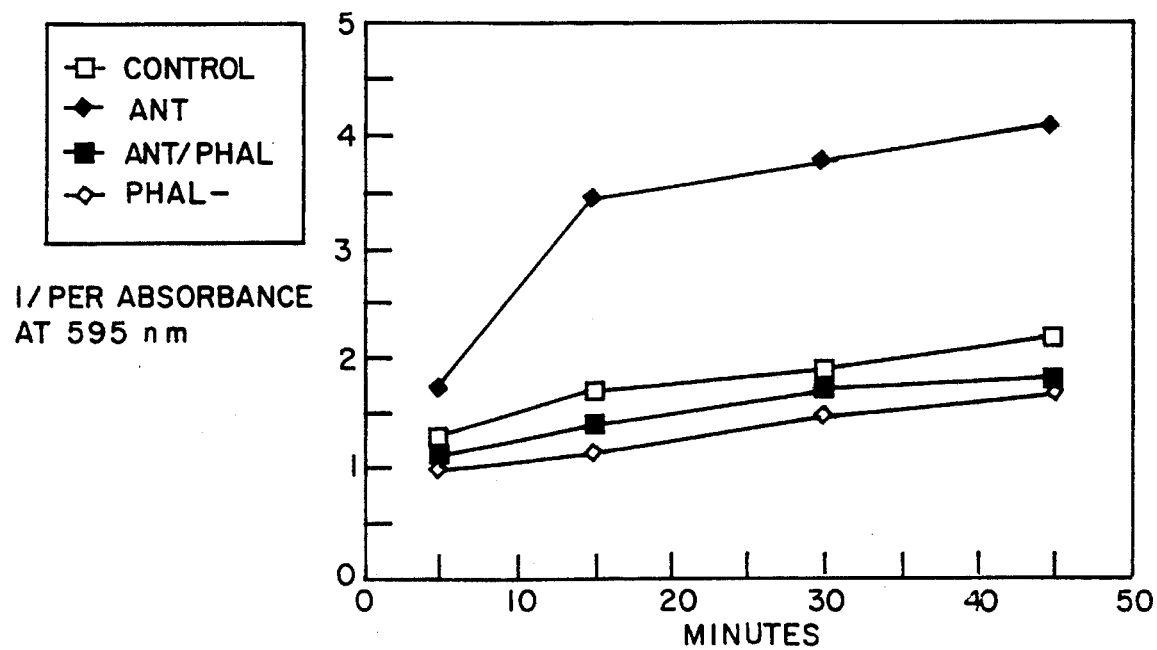
FIG. 2 is a graph illustrating the improvement in endothelial barrier function as a consequence of Phallin A administration.

The prepared aliquots of BAEC-covered microcarrier beads were individually combined with 1 uM of Phallin A, 1 uM of phalloidin, and a 1 uM to 1 uM ratio of Phallin A and phalloidin. The experimental controls received only DME without any phalloidin treatment whatsoever. TBA was added to each test aliquot and the permeability assay conducted in the manner described above. Centrifugation and test of supernatants was performed at 30 minutes following the initial addition of each test substance to each test aliquot of BAEC-covered beads. The results are graphically illustrated by FIG. 2. Clearly, the addition of Phallin A at a concentration of 1 uM improves resistance to permeability in endothelial cells and markedly increases cell barrier function in comparison to untreated controls and the mixture of phalloidin and Phallin A.

The present invention is not to be limited in scope nor restricted in form except by the claims appended hereto.

What we claim is:

1. A method for therapeutically reducing lung endothelial permeability in a living subject, said method comprising the step of:

intravenously administering an effective amount of an antamanide compound to the living subject after occurrence of an increased endothelial permeability to fluids and protein in the lung, said antamanide compound having the formula

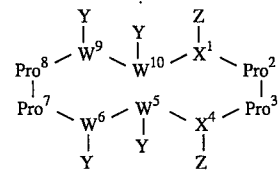

wherein W individually is an amino acid having at least one ring structure comprised of not more than 6 carbon atoms;

X individually is an acrylic amino acid comprised of 3–9 carbon atoms;

Y individually is omittable entirely but when present is selected from the group consisting of hydrogen, a hydroxyl group, a halogen, and a hydrocarbon moiety; and;

Z individually is omittable entirely but when present is selected from the group consisting of hydrogen, a halogen, and a hydrocarbon moiety.

2. A method for prophylactically treating inflammatory edema in the kidney as occurs with increased endothelial permeability to fluids and proteins in a living subject, said method comprising the step of:

intravenously administering an effective amount of an antamanide compound to the living subject before occurrence of the inflammatory kidney edema, said antamanide compound having the formula

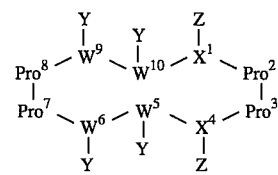

wherein W individually is an amino acid having at least one ring structure comprised of not more than 6 carbon atoms;

X individually is an acrylic amino acid comprised of 3–9 carbon atoms;

Y individually is omittable entirely but when present is selected from the group consisting of hydrogen, a hydroxyl group, a halogen, and a hydrocarbon moiety; and;

Z individually is omittable entirely but when present is selected from the group consisting of hydrogen, a halogen, and a hydrocarbon moiety.

3. A method for therapeutically reducing lung endothelial permeability in a living subject, said method comprising the step of:

intravenously administering an effective amount of an antamanide compound to the living subject after occurrence of an increased endothelial permeability to fluids and protein in the lung, said antamanide compound having the formula

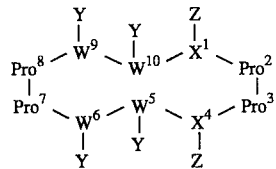

wherein W individually is an amino acid having a benzene ring in its structure;
X individually is an amino acid selected from the group consisting of valine, alanine, leucine, and isoleucine;
Y individually is omittable entirely but when present is selected from the group consisting of hydrogen, a hydroxyl group, a halogen, and a hydrocarbon moiety; and;
Z individually is omittable entirely but when present is selected from the group consisting of hydrogen, a halogen, and a hydrocarbon moiety.

4. A method for prophylactically treating inflammatory edema in the kidney as occurs with increased endothelial permeability to fluids and proteins in a living subject, said method comprising the step of:
intravenously administering an effective amount of an antamanide compound to the living subject before occurrence of the inflammatory kidney edema, said antamanide compound having the formula

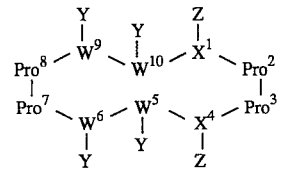

wherein W individually is an amino acid having a benzene ring in its structure;
X individually is an amino acid selected from the group consisting of valine, alanine, leucine, and isoleucine;
Y individually is omittable entirely but when present is selected from the group consisting of hydrogen, a hydroxyl group, a halogen, and a hydrocarbon moiety; and;
Z individually is omittable entirely but when present is selected from the group consisting of hydrogen, a halogen, and a hydrocarbon moiety.

5. The method as recited in claim 1, 2, 3, or 4 wherein said antamanide compound is naturally occurring.

6. The method as recited in claim 1, 2, 3, or 4 wherein said antamanide compound is synthetically generated.

* * * * *